United States Patent
Barrett et al.

(10) Patent No.: US 11,261,414 B2
(45) Date of Patent: Mar. 1, 2022

(54) APPARATUS FOR RECONFIGURATION OF COMPONENTS IN A MICROPHYSIOLOGICAL SYSTEM

(71) Applicants: Arizona Board of Regents on Behalf of the University of Arizona, Tucson, AZ (US); Universite du Luxembourg, Luxembourg (LU)

(72) Inventors: Matthew Barrett, Chandler, AZ (US); Marc Pol Mac Giolla Eain, Chandler, AZ (US); Paul Wilmes, Bettembourg (LU); Frederic Zenhausern, Chandler, AZ (US)

(73) Assignees: Arizona Board of Regents on Behalf of the University of Arizona, Tucson, AZ (US); Universite du Luxembourg, Luxembourg (LU)

( * ) Notice: Subject to any disclaimer, the term of this patent is extended or adjusted under 35 U.S.C. 154(b) by 267 days.

(21) Appl. No.: 16/348,835

(22) PCT Filed: Nov. 14, 2017

(86) PCT No.: PCT/US2017/061602
§ 371 (c)(1),
(2) Date: May 9, 2019

(87) PCT Pub. No.: WO2018/090035
PCT Pub. Date: May 17, 2018

(65) Prior Publication Data
US 2019/0345431 A1 Nov. 14, 2019

Related U.S. Application Data

(60) Provisional application No. 62/421,833, filed on Nov. 14, 2016.

(51) Int. Cl.
*C12M 1/00* (2006.01)
*C12M 3/06* (2006.01)
(Continued)

(52) U.S. Cl.
CPC ............ *C12M 23/38* (2013.01); *C12M 23/16* (2013.01); *C12M 23/46* (2013.01); *C12M 25/02* (2013.01)

(58) Field of Classification Search
None
See application file for complete search history.

(56) References Cited

U.S. PATENT DOCUMENTS

| 4,072,577 A | * | 2/1978 | Hirshaut | ................ C12M 23/32 435/252.1 |
| 6,054,100 A | * | 4/2000 | Stanchfield | .......... B01J 19/0046 422/534 |

(Continued)

FOREIGN PATENT DOCUMENTS

| CN | 204369902 | 6/2015 |
| WO | WO 2013/139798 | 9/2013 |

(Continued)

OTHER PUBLICATIONS

Abbeele et al. (2010) "Microbial Community Development in a Dynamic Gut Model Is Reproducible, Colon Region Specific, and Selective for Bacteroidetes and Clostridium Cluster IX," Appl Environ Microbiol 76(15): 5237.-5246.
(Continued)

*Primary Examiner* — Holly Kipouros
(74) *Attorney, Agent, or Firm* — Leydig, Voit & Mayer, Ltd.

(57) ABSTRACT

Provided herein is a microphysiological system that may be used in various cell culture applications and biological system studies, that facilitates co-culture, monitoring, and
(Continued)

study of functional interactions among different types of cellular and biological materials under various environmental conditions. The system is configured for fast assembly and disassembly, thereby minimizing damage or contamination of the biological materials and environmental conditions inside the system. The system comprises a base, a lid, and a plurality of clamps that are connected to the base and the lid. The base has a recess surface for receiving cell culture support layers. The lid has a stepped surface configured to exert a contact force to a top layer of one or more cell culture support layers during use. The clamp involves an engagement mechanism that generates a contact force allowing for sealing of the cell culture support layers in a manner that minimizes leakage of fluids.

23 Claims, 12 Drawing Sheets

(51) Int. Cl.
   *C12M 3/00* (2006.01)
   *C12M 1/12* (2006.01)

(56) References Cited

U.S. PATENT DOCUMENTS

| | | | |
|---|---|---|---|
| 6,379,626 B1* | 4/2002 | Munson | B01J 19/0046 422/129 |
| 9,844,780 B2* | 12/2017 | Lee | B01L 3/50273 |
| 2007/0231887 A1 | 10/2007 | McGrath et al. | |
| 2011/0174820 A1* | 7/2011 | Giles | B01L 3/508 220/315 |
| 2015/0072413 A1 | 3/2015 | Zenhausern et al. | |
| 2015/0299631 A1 | 10/2015 | Prabhakarpandian et al. | |
| 2015/0329816 A1* | 11/2015 | Owens | C12M 23/38 435/298.2 |
| 2017/0227525 A1 | 8/2017 | Griffith et al. | |
| 2018/0085726 A1* | 3/2018 | Sugiura | C12M 23/16 |
| 2018/0209731 A1* | 7/2018 | Knight | A01N 1/0252 |

FOREIGN PATENT DOCUMENTS

| | | |
|---|---|---|
| WO | WO 2013/144253 | 10/2013 |
| WO | WO 2014/016379 | 1/2014 |
| WO | WO 2016/189142 | 12/2016 |
| WO | WO 2017/091718 | 6/2017 |
| WO | WO 2017/096296 | 6/2017 |

OTHER PUBLICATIONS

Barranco et al. (1983) "Establishment and Characterization of an in Vitro Model System for Human Adenocarcinoma of the Stomach," Cancer Res 43(4): 1703-1709.
Becker et al. (2000) "Polymer microfabrication methods for microfluidic analytical applications," Electrophoresis 21(1): 12-26.
Coconnier et al. (1992) "Protein-mediated adhesion of Lactobacillus acidophilus BG2FO4 on human enterocyte and mucus-secreting cell lines in culture," Appl Environ Microbiol 58(6): 2034-2039.
Eain et al. (Feb. 2017) "Engineering Solutions for Representative Models of the Gastrointestinal Human-Microbe Interface," Engineering 3(1): 60-65.
Estes et al. (2009) "Isolation of prostate cancer cell subpopulations of functional interest by use of an on-chip magnetic bead-based cell separator," J Micromechanics Microengineering 19: 95015.
Flint et al. (2012) "The role of the gut microbiota in nutrition and health" Nat Rev Gastroenterol Hepatol 9: 577-589.
Fritz et al. (2013) "From meta-omics to causality: experimental models for human microbiome research," Microbiome 1: 14, 15 pages.
Gibson et al. (1988) "Use of a three-stage continuous culture system to study the effect of mucin on dissimilatory sulfate reduction and methanogenesis by mixed populations of human gut bacteria," Appl Environ Microbiol 54(11): 2750-2755.
Goodman et al. (2011) "Extensive personal human gut microbiota culture collections characterized and manipulated in gnotobiotic mice," PNAS 108(15): 6252-6257.
Hidalgo et al. (1989) "Characterization of the human colon carcinoma cell line (Caco-2) as a model system for intestinal epithelial permeability," Wiley, Hoboken, NJ, ETATS-UNIS.
Hopwood et al. (2010) "Integrated microfluidic system for rapid forensic DNA analysis: sample collection to DNA profile," Anal Chem 82(16): 6991-6999.
International Search Report and Written Opinion, dated Feb. 27, 2018, corresponding to International Patent Application No. PCT/US2017/061602, 7 pages.
Kashyap et al. (2013) "Complex interactions among diet, gastrointestinal transit, and gut microbiota in humanized mice," Gastroenterology 144(5): 967-977.
Lesuffleur et al. (1990) "Growth Adaptation to Methotrexate of HT-29 Human Colon Carcinoma Cells Is Associated with Their Ability to Differentiate into Columnar Absorptive and Mucus-secreting Cells," Cancer Res 50(19): 6334-6343.
Lukovac et al. (2014) "Differential Modulation by Akkermansia muciniphila and Faecalibacterium prausnitzii of Host Peripheral Lipid Metabolism and Histone Acetylation in Mouse Gut Organoids," Amer. Soc. Mbio. 5(4): e01438-14, pp. 1-10.
MacFarlane et al. (2005) "Colonization of Mucin by Human Intestinal Bacteria and Establishment of Biofilm Communities in a Two-Stage Continuous Culture System," Appl Environ Microbiol 71(11): 7483-7492.
Molly et al. (1993) "Development of a 5-step multichamber reactor as a simulation of the human intestinal microbial ecosystem," Appl Microbiol Biotechnol 39: 254-258.
Nuenen et al. (2003) "The Effect of Various Inulins and Clostridium difficile on the Metabolic Activity of the Human Colonic Microbiota in vitro," Microb Ecol Health Dis 15: 137-144.
Pflughoeft & Versalovic (2011) "Human Microbiome in Health and Disease," Annu Rev Pathol 7: 99-122.
Rodes et al. (2011) "Transit time affects the community stability of *Lactobacillus* and *Bifidobacterium* species in an in vitro model of human colonic microbiotia," Artif Cells Blood Substit Immobil Biotechnol 39: 351-356.
Romano et al. (1988) "Human cell line for study of damage to gastric epithelial cells in vitro," J Lab Clin Med 111 (4): 430-440.
Sekiguchi et al. (1978) "Establishment of cultured cell lines derived from a human gastric carcinoma," Jpn J Exp Med 48(1): 61-68.
Shah et al. (2011) "Microfluidic bioreactors for culture of non-adherent cells," Sensors Actuators B Chem 156(2): 1002-1008.
Shah et al. (May 2016) "A microfluidics-based in vitro model of the gastrointestinal human-microbe interface," Nat. Commun. 7: 11535, pp. 1-15.
Shen et al. (2006) "DNA Diffusion in Mucus: Effect of Size, Topology of DNAs, and Transfection Reagents," Biophys J 91(2): 639-644.
Skolimowski et al. (2010) "Microfluidic dissolved oxygen gradient generator biochip as a useful tool in bacterial biofilm studies," Lab Chip 10(16): 2162-2169.
Vesterlund et al. (2006) "*Staphylococcus aureus* adheres to human intestinal mucus but can be displaced by certain lactic acid bacteria," Microbiology 152: 1819-1826.
Wichmann et al. (2013) "Microbial modulation of energy availability in the colon regulates intestinal transit," Cell Host Microbe 14: 582-590.
Yamashita et al. (2002) "New and better protocols for a short-term Caco-2 cell culture system," J Pharm Sci 91(3): 669-679.

* cited by examiner

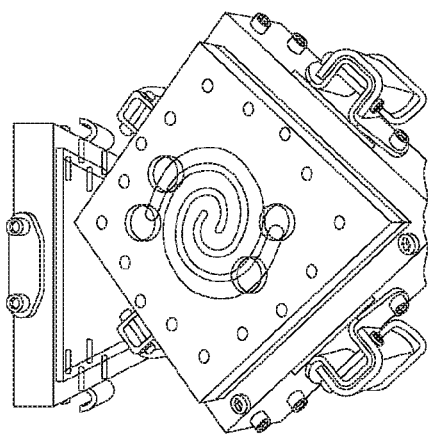
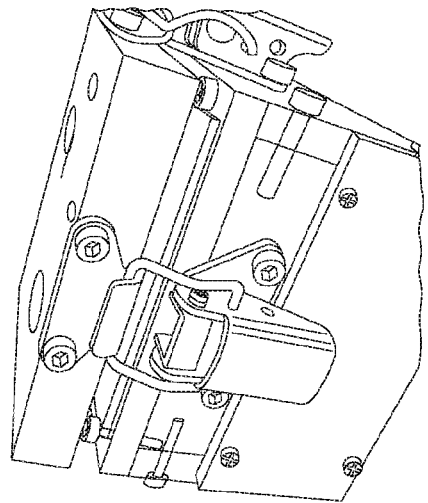
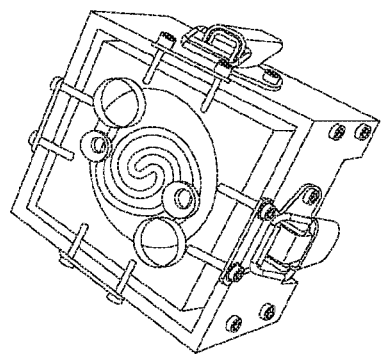
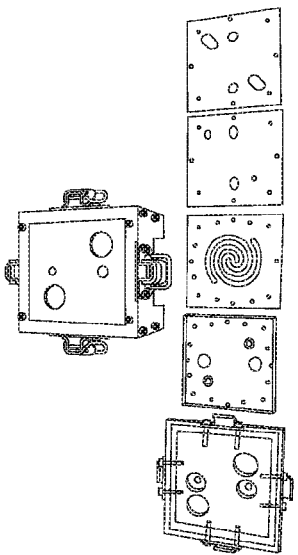
Apparatus for the assembly and disassemble using a clamping mechanism allowing multiple layers packaging and reconfiguration.
FIG. 9

Close-up on the components using alignment pins for the assembly.

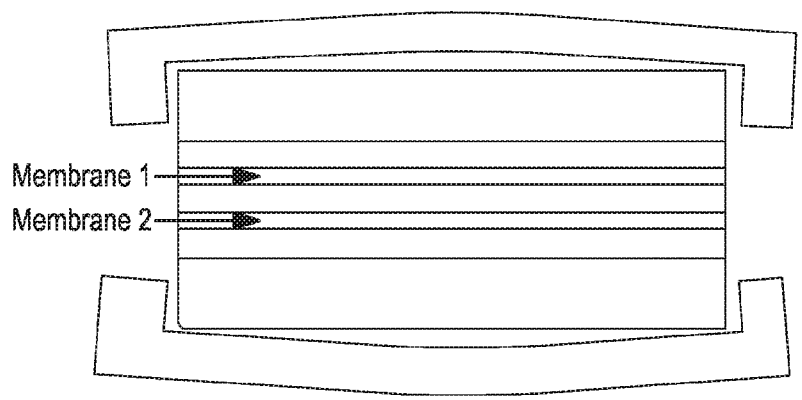
(top) Warping of the lid and the base without step and recess features such that contact pressure is not uniform
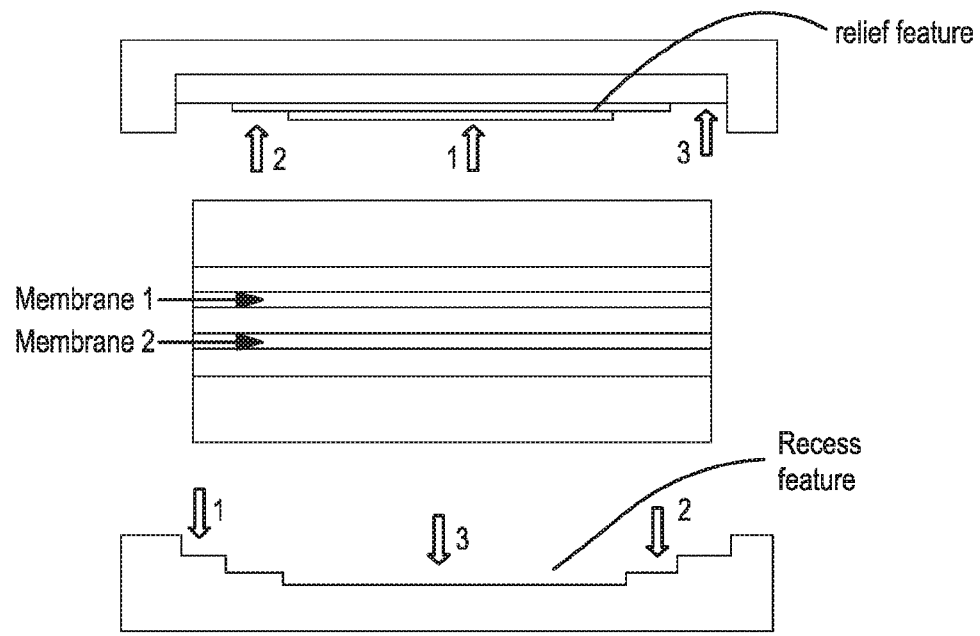
(bottom) Step and recess features in the lid and the base provide uniform contact pressure during clamping
FIG. 12

APPARATUS FOR RECONFIGURATION OF COMPONENTS IN A MICROPHYSIOLOGICAL SYSTEM

CROSS-REFERENCE TO RELATED APPLICATIONS

This application is a U.S. National Stage Application filed under 35 U.S.C. § 371 of International Application No. PCT/US2017/061602, filed Nov. 14, 2017, which claims benefit of and priority to U.S. Provisional Pat. App. No. 62/421,833 filed Nov. 14, 2016, which is hereby incorporated by reference in its entirety, to the extent not inconsistent herewith.

BACKGROUND OF INVENTION

Useful 3D in vitro devices for studying the functional interactions of the microbial ecosystems on the host tissue requires individually and reliable accessing of each of the multiple modules and components of the device, including for humans. This is important for a number of reasons, including: preparing the various biological compartments to receive the relevant biological materials; setting up specific conditions; controlling operating conditions; and accessing relevant output materials, even when experiments are ongoing. A modular apparatus allows for tuning and controlling of the aforementioned experimental variables. Conventional modular devices are generally held together using a sufficient number of nuts and bolts around the effective area of the microfluidic bioreactor elements for experimentation, including in a circular pattern. Typically in vitro microphysiological systems require multiple chambers of cellular culture and a perfusion chamber for nutrients, including as described in any of PCT Pub. Nos. WO2013EP055712, WO2013EP065718; and WO201344253 and U.S. Provisional App. No. 62/166,940 (filed May 27, 2015) and PCT App. No. PCT/EP2016/062024 (filed May 27, 2016), each titled "Cell Culture Apparatus and Culture Methods Using Same".

However, while attempting to access the internal cellular components and biomolecular materials directly, the manner in which the device is fluidically sealed, particularly adjacent components contained within the device separating different biological systems, will take time and skill by a user. For example, the time to disassemble the device can be substantial, including 10 or 15 minutes or more for the most skilled user. The large amount of time is associated with having to handle each of the large number of nut and bolt fasteners, resulting in a significant time and effort with attendant disadvantages. The disadvantages extend beyond mere inconvenience, and include exposure to unwanted oxygen and other potential environmental contaminants that can penetrate and damage the cellular and biological materials, thereby altering biology of the system and affecting test reproducibility, especially when performing integrated omics analyses (e.g. metabolomics), accuracy and overall quality of data results. A faster means of disassembly that does not adversely impact device functionality and fluidic integrity is needed to ensure reliable test results and accurate biological modeling and test integrity.

SUMMARY OF THE INVENTION

Provided herein are various novel devices that can be reconfigured in multiple forms suitable for achieving modular assembly and disassembly of a microfluidic-based system that facilitates co-culture, monitoring and study of functional interactions among different types of cellular and biological materials under various environmental conditions. The devices described herein can minimize risk of contamination and improve reproducibility of the system while presenting a user with a readily manipulated and accessible system for testing or analysis of biological systems and materials, including cell cultures. The technical problem described herein of complex and time-consuming device disassembly and access to various modules is solved by use of a specially configured lid and base configuration with specially positioned clamps connected to the lid and base. The claim mechanisms replace conventional fasteners corresponding to thread and nut fastening systems without sacrificing reliable fluidic sealing.

Provided herein are microphysiological systems, including a device to facilitate cell culturing. The systems may be based on a buckle clamp stage-like apparatus that facilitate a faster assembly and disassembly of a modular microfluidic microbiome system, organ-on-chip or other microphysiological systems. Examples of devices compatible with the instant systems include any one or more of the systems described in PCT Pub Nos. WO2013EP055712, WO2013EP065718, and WO201344253, U.S. Provisional App. No. 62/166,940 (filed May 27, 2015) and PCT App. No. PCT/EP2016/062024 (filed May 27, 2016), each titled "Cell Culture Apparatus and Culture Methods Using Same", and each of which are specifically incorporated by reference to the extent not inconsistent herewith for any of the cell culture layers, biological models, fluidic controllers, sensors, actuators, and various operating parameters.

Claim examples of microphysiological systems and related methods include any one or more of the following:

1. A microphysiological system comprising: a base having a recess surface for receiving a cell culture support layer; a lid having a stepped surface configured to exert a contact force to a top layer of a plurality of cell culture support layers during use; and a clamp operably connected to each of said base and said lid, said clamp having a clamp engagement mechanism to generate said contact force and fluidically seal said plurality of cell culture support layers.

2. The microphysiological system of claim 1, having a top surface, a bottom surface, and a plurality of side surfaces extending between said top and bottom surfaces to form an enclosure volume, the system further comprising connectors positioned on a single surface to connect with fluid conduits, pumps, actuators, sensors, or any combination thereof.

3. The microphysiological system of claim 1 or 2, wherein said clamp comprises: a top clamp component connected to said lid, a bottom clamp component connected to said base, and said clamp engagement mechanism is operably connected to said top clamp component and said bottom clamp component to generate said contact force upon engagement.

4. The microphysiological system of any of claims 1-3, wherein said clamp engagement mechanism comprises a buckle.

5. The microphysiological system of any of claims 1-4 comprising a plurality clamps distributed around a perimeter of said base and lid to generate a uniform contact pressure exerted on said top layer of said plurality of cell culture support layers.

6. The microphysiological system of any of claims 1-5, wherein said base and lid are multi-sided and each base-lid pair side has a clamp connected thereto.

7. The microphysiological system of any of claim 1-6, wherein each of said base and lid have sides with a side length, wherein said clamp extends over at least a central 25% of said side length.

8. The microphysiological system of any of claims 1-7, wherein: said top clamp component comprises a holder with a plurality of orifices each configured to receive a fastener to connect said holder to a side edge of said lid; said bottom clamp component comprises a buckle with a plurality of orifices each configured to receive a fastener to connect said bottom clamp to a side edge of said base; and wherein said buckle is configured to reversibly engage with said holder and provide a rapid disassembly to minimize an adverse biological effect on cultured biological cells during use.

9. The microphysiological system of any of claims 1-8, wherein said lid stepped surface comprises: a relief feature having a relief height that is greater than or equal to 0.05 mm and less than or equal to 0.3 mm; and/or a ratio of said relief height to thickness of the substrates, from which the relief height extends, that is greater than 0.01 and less than 0.1.

10. The microphysiological system of any of claims 1-9, wherein said base recess surface comprises: a step recess depth that is greater than or equal to 0.05 mm and less than or equal to 0.3 mm; and/or a ratio of said recess height to thickness of the substrate, from which the recess height extends, that is greater than 0.01 and less than 0.1.

11. The microphysiological system of any of claims 1-10, wherein: said lid stepped surface and said base recess surface are configured to provide a deflection angle of said lid, said base, or both, that is greater than 0.1 degrees and less than 10 degrees and to maintain a uniform contact pressure against said cell culture support layers during use.

12. The microphysiological system of any of claims 1-11 having a plurality of step surfaces and/or a plurality of recess surfaces.

13. The microphysiological system of any of claims 1-12 having a footprint area less than or equal to 6400 mm² or less than or equal to 10 inch×10 inch square).

14. The microphysiological system of any of claims 1-13 having a total assembled height less than or equal to 90 mm (3.5 inches).

15. The microphysiological system of any of claims 1-14 further comprising a plurality of legs connected to or extending from said base to support said apparatus on a support surface.

16. The microphysiological system of any of claims 1-15 comprising a four-sided lid and corresponding four-sided base, with a clamp operably connected to each pair of lid and base sides.

17. The microphysiological system of any of claims 1-16, configured to receive a plurality of cell culture support layers that are circular, ellipsoid, rectangular or square.

18. The microphysiological system of any of claims 1-17, wherein said plurality of cell culture support layers comprises at least three cell cultivation layers and at least two membranes, wherein one membrane separates adjacent cell cultivation layers, wherein said cell culture layers and membranes have a total thickness that is less than or equal to 3 mm.

19. The microphysiological system of any of claims 1-18, wherein said plurality of cell culture layers comprises a lock-and-key alignment feature to align and fixably position each of said layers.

20. The microphysiological system of any claims 1-19, having an assembly and/or disassembly time that is less than 5 minutes. The unique configuration of the base and lid, in combination with the reliable clamp engagement mechanism provides this fast assembly/disassembly time.

21. The microphysiological system of any of claims 1-20, further comprising access ports through a top surface of said lid for operably connecting biological sensors, controllers and/or fluidic inlets and outlets to said cell culture support layers.

22. The microphysiological system of any of claims 1-21, wherein the clamps are configured to facilitate optical imaging of cells on at least one of the cell culture support layers, optionally during use of the system, after partial disassembly of the system, or after complete removal of the cell culture support layer from the system.

23. A method of cell culturing comprising the steps of: providing a microphysiological system of any of claims 1-22; placing a plurality of cell culture support layers in said base; clamping said base to said lid; and introducing biological fluid and biological cells to said cell culture support layers, wherein said clamping step fluidically seals adjacent layers of said plurality of cell culture support layers to avoid unwanted leakage out of channels or chambers formed between adjacent cell culture support layers.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 8. Comparison of resultant system sizes for press-style (top image) versus the instant buckle-style clamp (bottom image). In addition, the buckle-style clamp maximizes accessibility to the top surface of the device, making it a convenient location for fluid conduits, connects, sensors and the like.

FIG. 9. Photographs of a microphysiological system (top left), showing close-up views of the buckle (top middle), interior positioned stack of cell culture support layers (top right), individual layers of the cell culture support layers and disconnected lid and base (bottom left), and lock-and-key alignment features (bottom right).

FIG. 12. Schematics illustrating the relief and recess features (not to-scale) in the base and the lid of the microphysiological system, and the benefits thereof. The top image illustrates the effect of not having relief and recess features in the base and the lid, whereby clamping of the system causes bowing in the center, and a non-uniform contact pressure on the cell culture support layers, risking unwanted leakage. The bottom image illustrates the relief and recess features of the base and the lid to minimize and prevent bowing and provide uniform contact pressure on the cell culture support layers, which prevents unwanted fluid leakage out of the system or between layers thereof. In addition, the geometric design ensures even for bowing or curvature of the lid there remains a reliable contact and pressure exertion, even on the middle region of the cell culture support layers.

DETAILED DESCRIPTION OF THE INVENTION

In general, the terms and phrases used herein have their art-recognized meaning, which can be found by reference to standard texts, journal references and contexts known to those skilled in the art. The following definitions are provided to clarify their specific use in the context of the invention.

"Operably connected" refers to a configuration of elements, wherein an action or reaction of one element affects another element, but in a manner that preserves each element's functionality.

"Membrane" refers to a semi-permeable layer that is permeable to a pre-determined class of fluids or particles, such as nucleic acids, proteins or small molecules for applications that collect metabolites or byproducts representative of the interactions or communication between the animal cells and the microbiota, and that are impenetrable by a pre-determined class of biological cells.

Microphysiological systems includes "cell culture apparatus" that can be used to grow, culture and study any number of cell types, including animal cells, bacterial cells, viruses and biochemically active agents.

"Cell culture support layer" refers to any layer within the microphysiological system, or cell culture apparatus, that assists in the function of the microphysiological system. Cell culture support layers include, but are not limited to, layers that involve lock-and-key alignment features, layers that allow for the introduction or removal of biological material, and layers that allow for the introduction or removal of liquid or gaseous fluids.

"Uniform contact pressure" refers to a force exerted onto a layer of the cell culture support layers that is relatively uniformly distributed over the entire surface area. Because pressure is a force per unit area, such a uniform force may be described as having a uniform pressure over the corresponding surface area that the force is exerted. In the instant devices, the specially constructed recess and/or step features, provides a platform for ensuring a uniform pressure onto the adjacent cell culture support layer. Uniform contact pressure may optionally be quantifiably defined, such as a maximum or minimum pressure point over a region of at least 90% of the surface that deviates by less than or equal to 20%, less than or equal to 10%, or less than or equal to 5% of the average pressure over the entire surface.

"Fluidic seal" or "fluidically sealed" refers to a combination of components or layers that confine fluid to a desired location. For example, a fluidically sealed cell culture support layer system refers to fluid that does not leak into the system, out of the system, or flow in an unwanted manner between adjacent layers. Of course, the system can tolerate minor leakage and remain functional.

Figure 1:
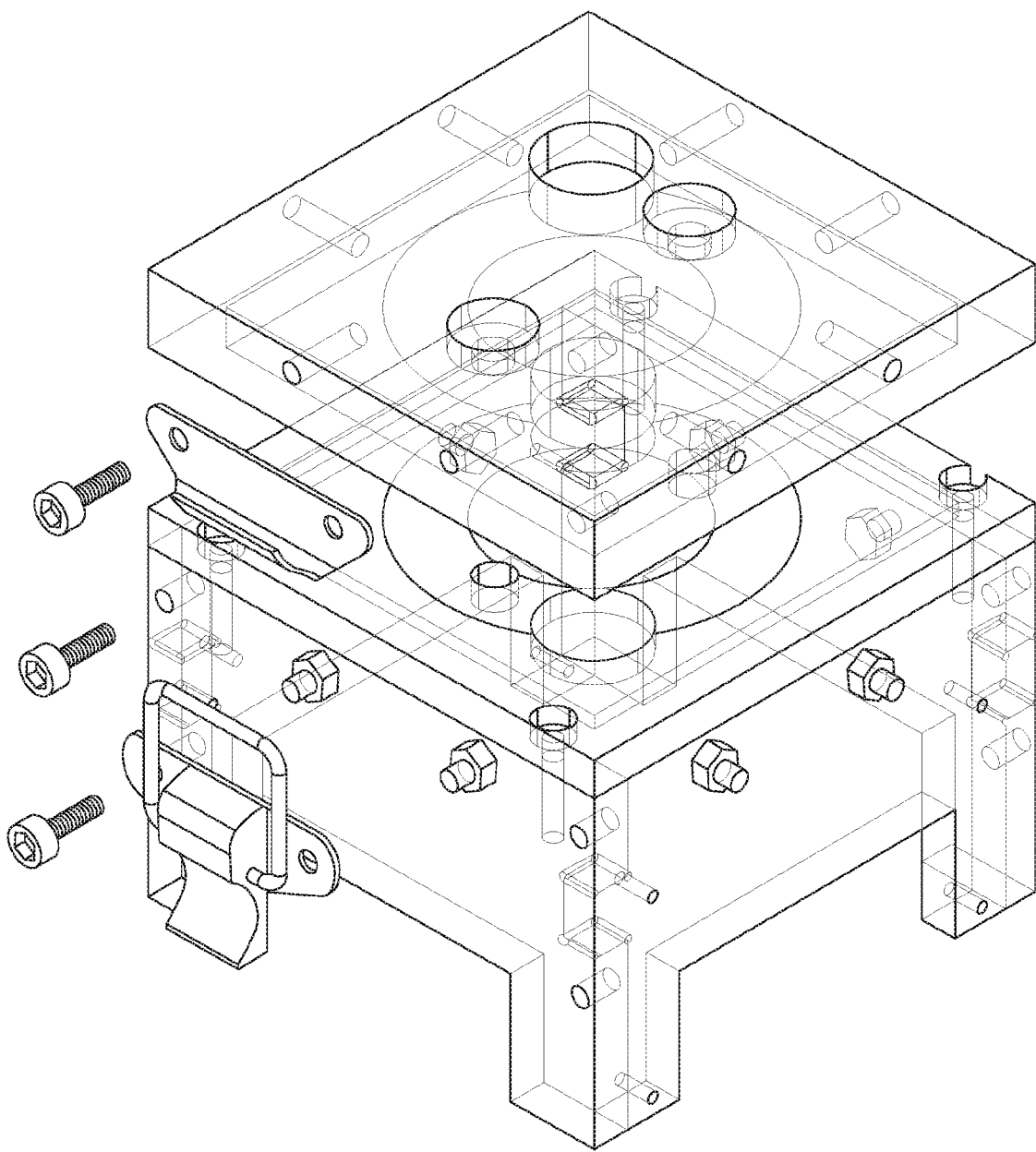
FIG. 1. Schematic of a microphysiological system showing the lid and base made of an optically transparent plastic, such as polycarbonate or COC (cyclic olefin copolymer). The clamp components are shown on one side of the device, with passages through the other sides of the lid and base illustrating that multiple clamps may be used. Fasteners may connect the top clamp component to the lid side and bottom clamp component to the base, with a quick-release rotatable clamp to tightly engage the lid and base. One clamp may be positioned on each of the four sides, with recess and relief features in the base and lid ensuring fluidic seal of culture support layers in the interior space formed by the base and lid. The clamp is illustrated as having stainless steel 3 mm bolts and stainless steel buckles. Of course, the clamps can formed from any number of materials, including but not limited to, plastic materials. Similarly, the clamps and various other components may be integrated with other portions of the system, such as by an injection molding process, as desired.
Figure 2:
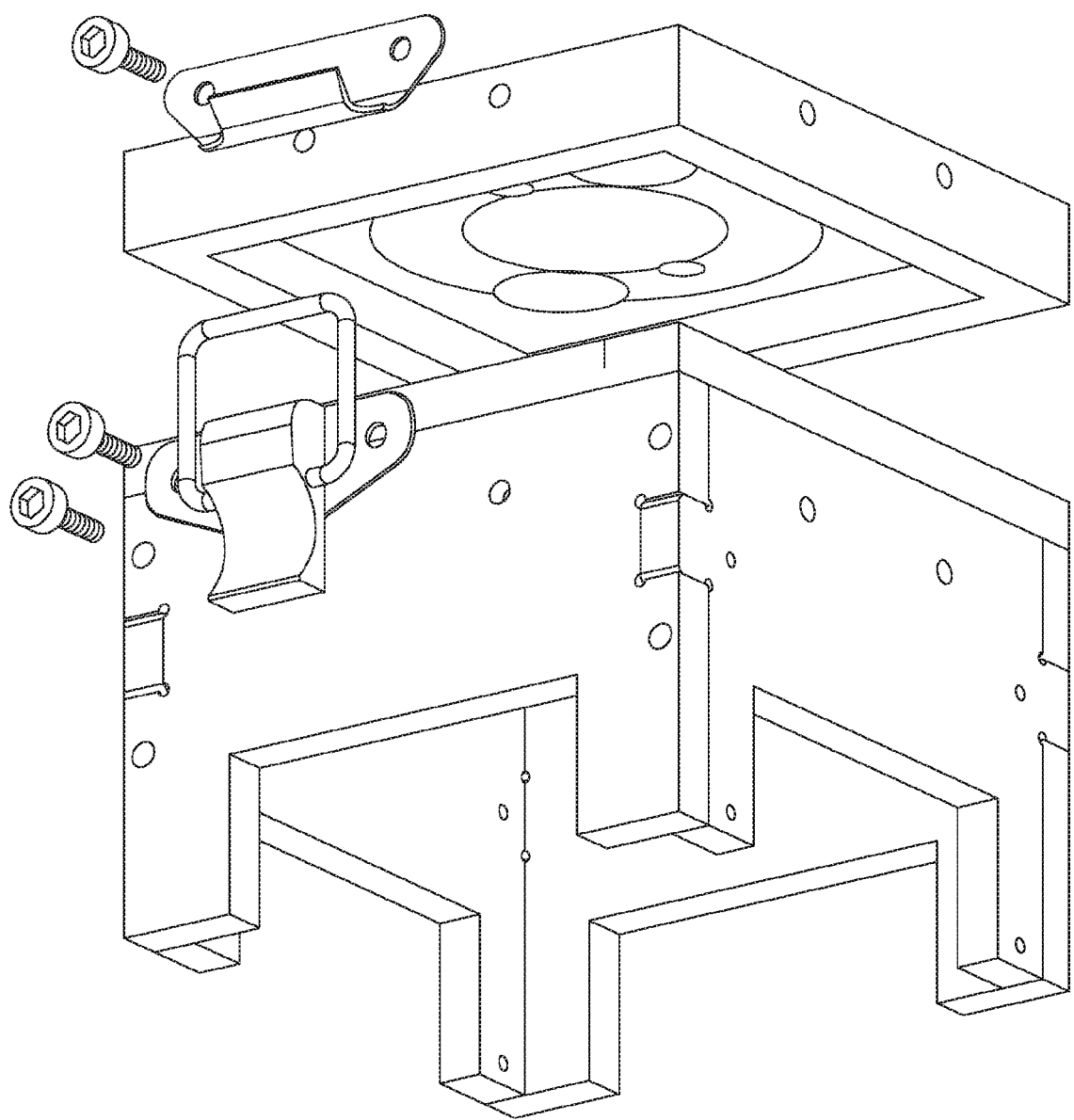
FIG. 2. Solid schematic view of the microphysiological system. The clamp components are shown on one side of the device as an example for illustrative purpose.
Figure 3:
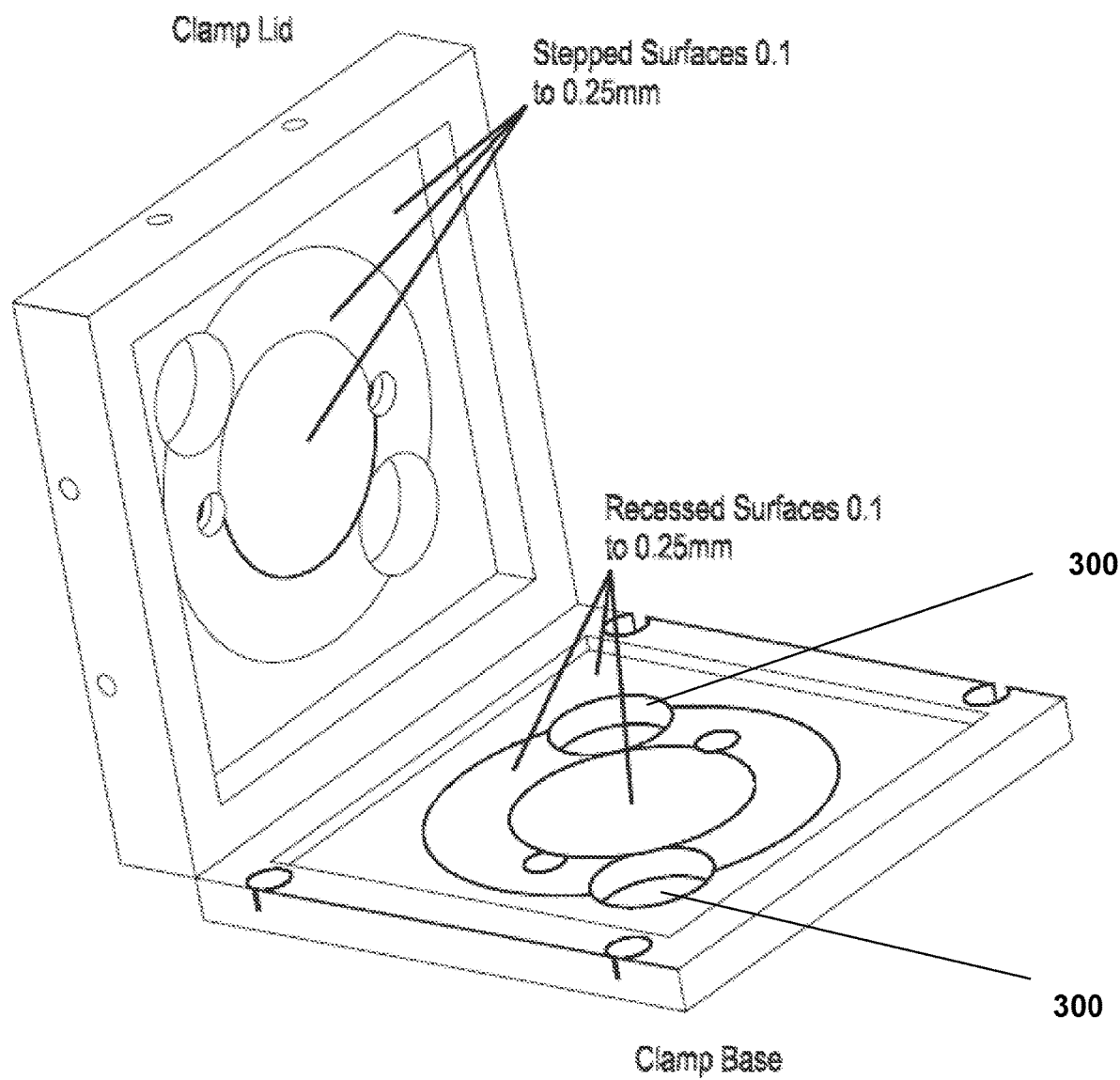
FIG. 3. Schematic illustration of the lid and top face of the base, particularly pointing out the step and recess features for reliable placement of, and force on, the cell culture support layers. The larger orifices provide connection of fluidic controllers, sensors and the like to the support layers connectors 300.
Figure 4:
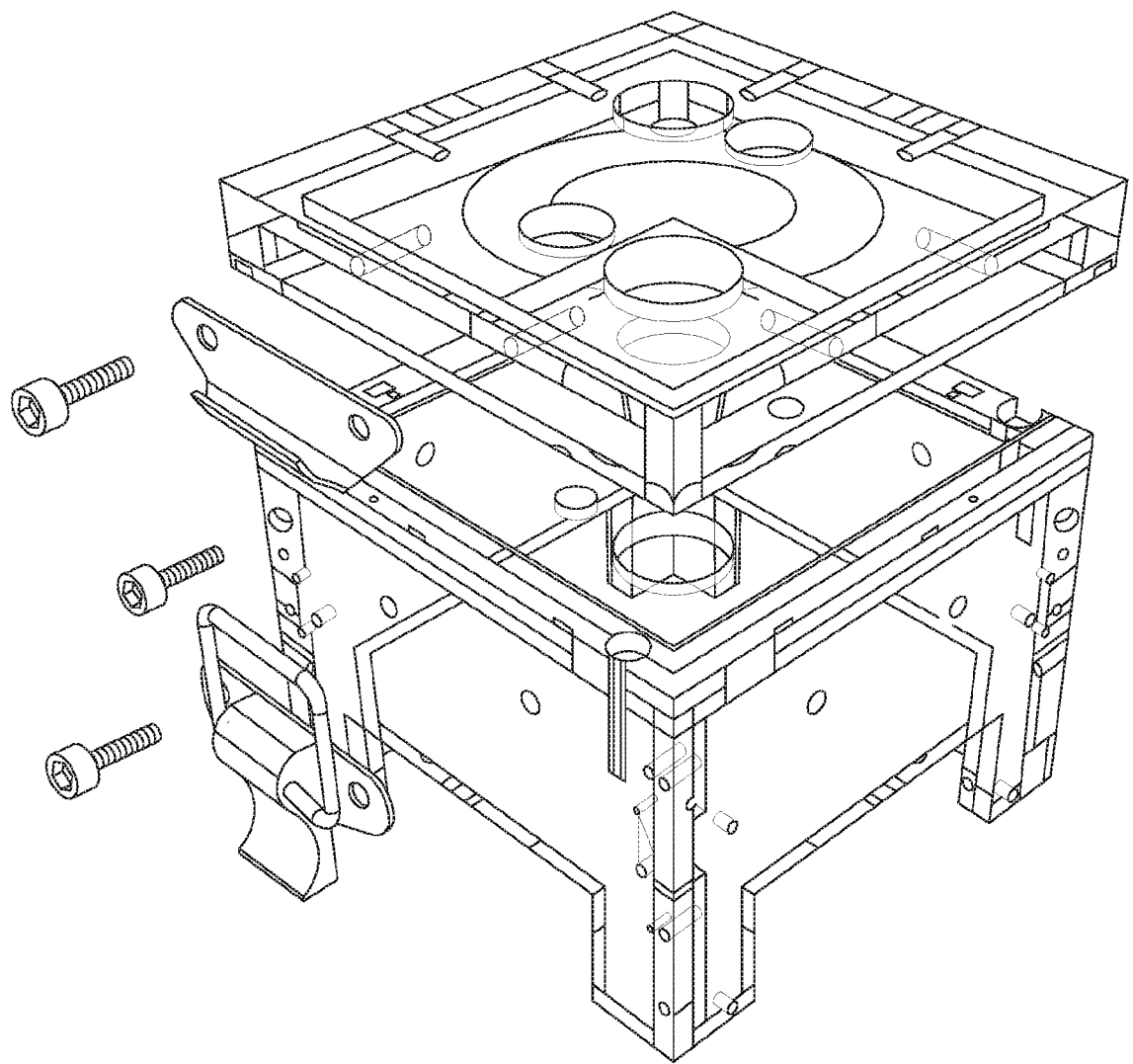
FIG. 4. Schematic of the microphysiological system, further illustrating various components, particularly the clamp components, which are shown on one side of the device as an example.
Figure 8:
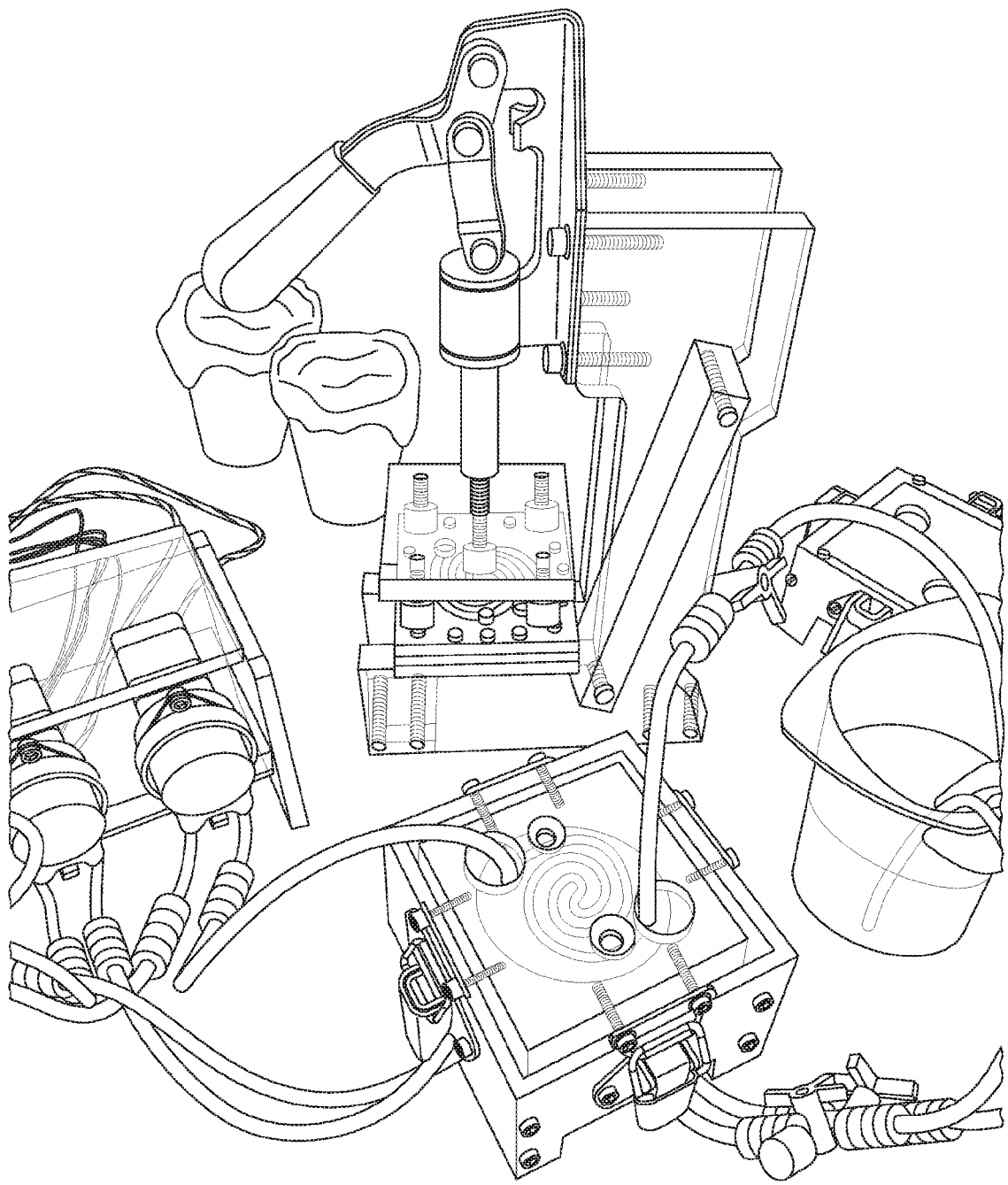

The system, and components thereof, are illustrated in FIGS. 1-4, including a base and lid with recess and stepped surfaces to hold a plurality of cell culture support layers (see, e.g., FIG. 9, bottom, left panel), and clamps (only one shown in FIGS. 1-2 to improve clarity; four shown in FIGS. 8-9).

Figure 5:
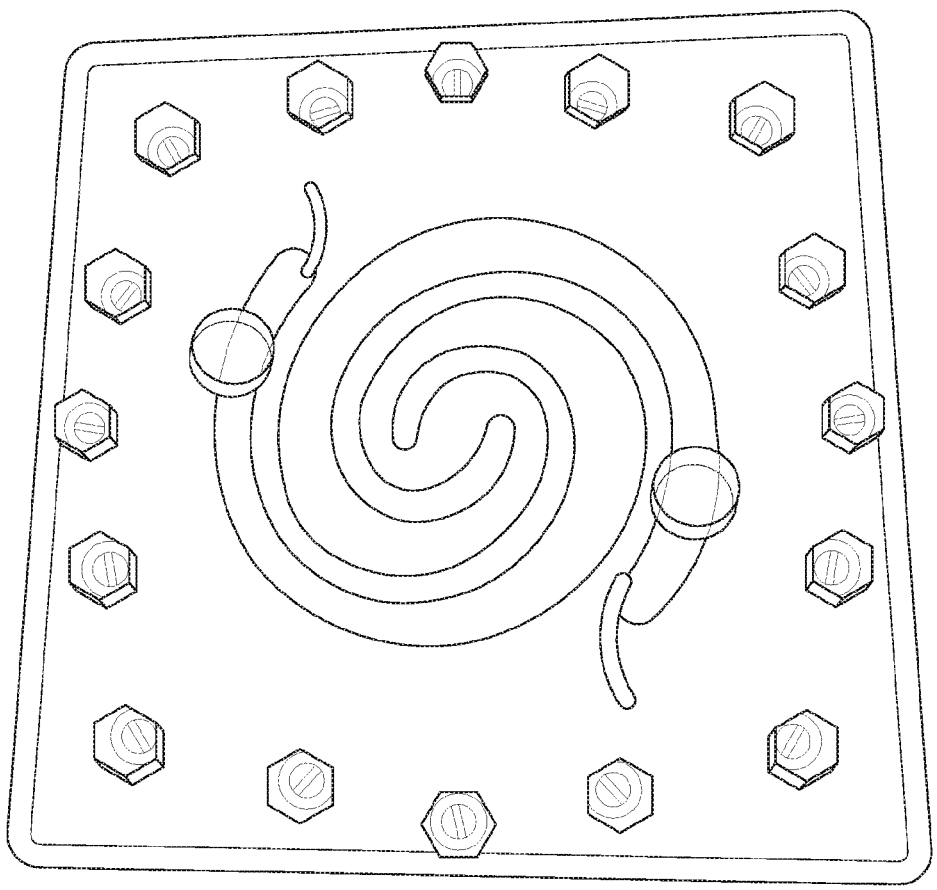
FIG. 5. A conventional cell culture device that is held together with a set of 16 M2 nuts-and-bolts arranged in a circular pattern to bond the multi-layer device and gaskets together to achieve a fluidic seal.

The original clamping system for the devices relied on a set of nuts and bolts to bond the multi-layer device and gaskets together (FIG. 5). It worked best to torque them all similarly to prevent leakage. The time involved was usually 15 to 20 minutes of placement and tightening. This was a large amount of time to spend under a bio-hood to prevent contamination while assembling the device.

Figure 6:
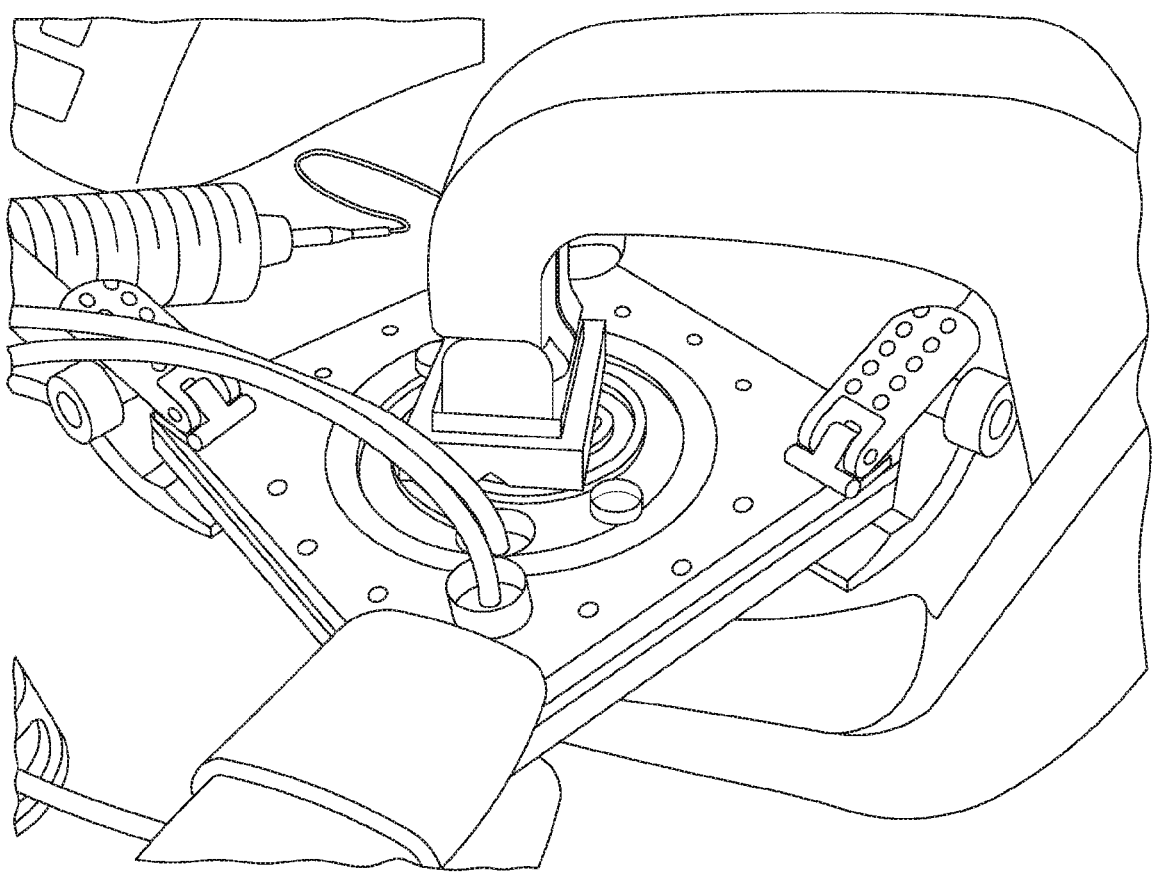
FIG. 6. A cell culture device, wherein a set of manual clamps exert a force to fluidically seal and/or find and remove fluid leakage points.
Figure 7:
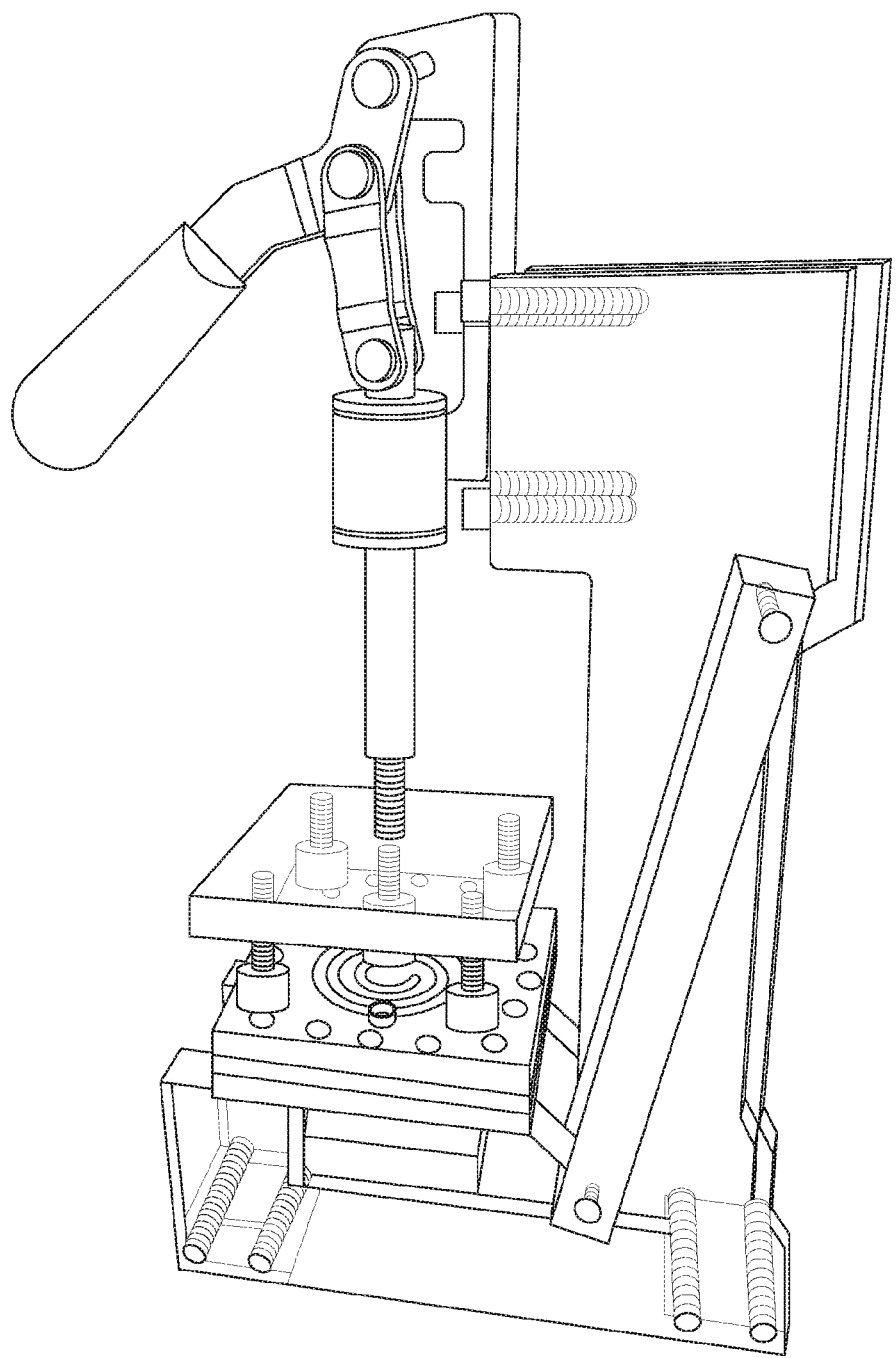
FIG. 7. Photograph of a cell culture device, fluidically sealed with a press-style clamp.

A first solution to this problem is a system with a press to apply the pressure evenly over the device surface, essentially pinching the multi-layers, holding them together and preventing leakage (FIG. 6). The device was successful, after a few iterations, finding the correct pressure points and the right amount of force necessary to pinch the system together. However, the system (FIG. 7) was much larger than originally planned and was quite cumbersome to handle while priming the multi-layer device. It also took up too much room in an incubator and, therefore, limited the quantity that could be run to two devices or, at most three with some inventive arrangements, for conventionally-sized incubators.

The instant microphysiological system, or cell culture apparatus, solves the problems associated with the original multi-layer closure system. It allows quick and easy assembly of the multi-layer device. With the use of recessed and stepped surfaces on the lid and base, the apparatus puts pressure where needed to solve leakage issue. A clamping mechanism applies an even and uniform pressure on the cell culture apparatus layers. The apparatus is compact (FIG. 8), allowing for more devices to be processed in a single incubator. Because of the quick assembly, there is less chance for contamination. It is easily handled and manipulated for being able to prime the device.

Figure 10:
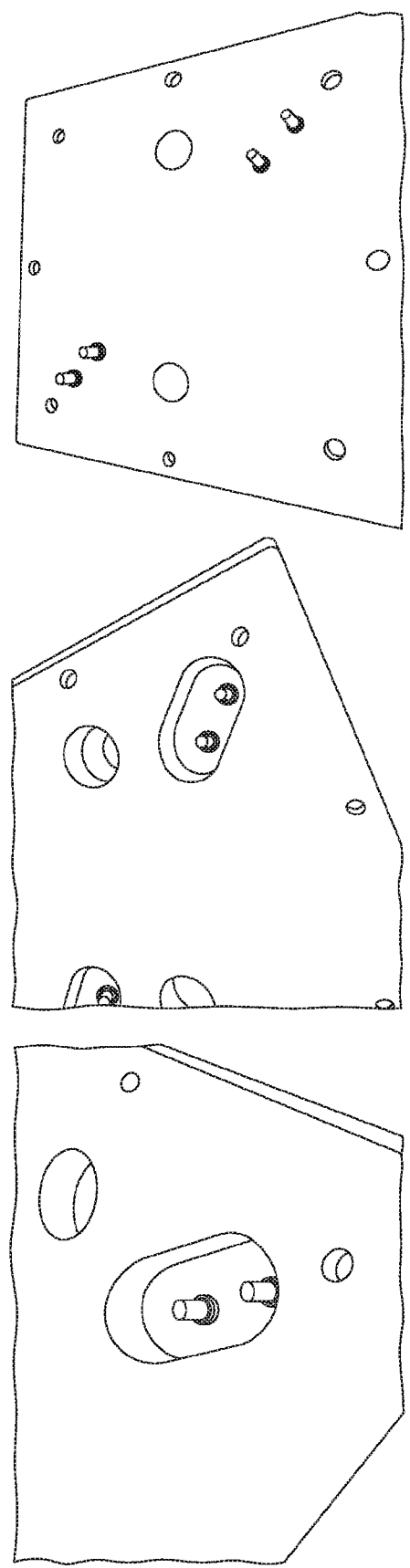
FIG. 10. Close-up of the lock-and-key alignment, illustrating pins for the assembly and alignment of the layers.

Multiple cell culture support layers (FIG. 9) are used to accurately align the cell culture the membrane and culture layers as well as apply even pressure onto the membrane and culture layers. The cell culture support layers assist in minimizing leakage of fluid and biological materials outside of the areas intended to contain said fluids and materials. For example, some cell culture support layers comprise lock-and-key alignment features (FIG. 10). The cell culture support layers also have access ports/holes for connecting biological sensors, controllers, and/or fluidic inlets and outlets (FIG. 8). Thin layer membranes that are difficult to handle reliably, may be handled with a vacuum accessory (FIG. 11).

Figure 11:
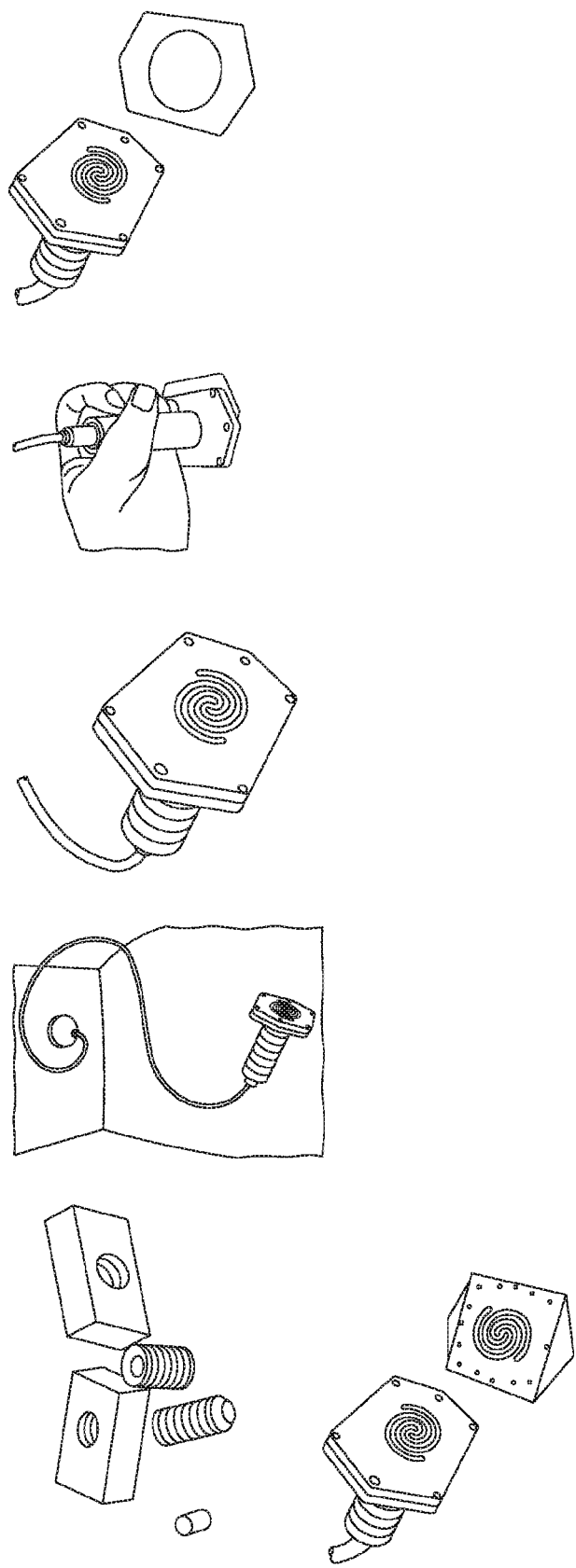
FIG. 11. A series of photographs illustrating a vacuum chuck accessory that assists the user in handling thin layer membranes during the assembly of the microphysiological system.

An accessory that uses vacuum (suction) assists the user in handling thin layer membranes during the assembly of the modular microphysiological system, or cell culture apparatus (FIG. 11).

The lid of the microphysiological system has relief features and the base of the microphysiological system has complimentary recess features that, upon clamping, are configured to generate pressure on areas of the multi-layer device to prevent leakage past the gaskets, between adjacent layers, etc. (FIG. 12). During clamping, the assembly of cell culture support layers is slightly bent because the center part of the lid presses the device down in the middle first, causing the outer edges of the device on the bottom plate to also press first. As the clamp is closed tighter, the next step on top presses down a bit further outward, and vice-versa, the bottom plate presses more on the same feature. The last step to contact the multi-layer device is the outer edge which presses down at the same time that the bottom center is contacting. The plastic material from which the base and the lid are made bends under the pressure of the clamps, so the step-and-recess feature takes advantage of this property from the plastic. Without the aforementioned relief-and-recess features, the pressure applied upon clamping would warp the lid as well as the top of the base, which may be made of plastic, such that there would be little or no pressure on the center of the assembly of cell culture support layers, thereby causing leakage through gaskets and across fluidic channels. The device is exemplified as having relief features on the lid and corresponding recess features on the base. Of course, the system may be configured for relief features on the base and corresponding recess features on the lid.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups are disclosed separately. Specific names of compounds are intended to be exemplary, as it is known that one of ordinary skill in the art can name the same compounds differently.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

REFERENCES

PCT Application WO2013EP055712, PCT Application WO2013EP065718, PCT Application WO201344253, U.S. Provisional Application 62/166,940.

We claim:

1. A microphysiological system comprising:
a plurality of cell culture support layers having a top layer;
a base having a recess surface for receiving said plurality of cell culture support layers;
a lid having a stepped surface configured to exert a contact force to said top layer of said plurality of cell culture support layers during use; and
a clamp operably connected to each of said base and said lid, said clamp having a clamp engagement mechanism to generate said contact force and fluidically seal said plurality of cell culture support layers;
wherein the clamp engagement mechanism comprises:
a top clamp component connected to said lid and a bottom clamp component connected to said base wherein said bottom and top clamp components directly engage with each other to directly clamp the base to the lid and generate said contact force having a uniform contact pressure exerted on said top layer of said plurality of cell culture support layers upon engagement.

2. The microphysiological system of claim 1, having a top surface, a bottom surface, and a plurality of side surfaces extending between said top and bottom surfaces to form an enclosure volume, the system further comprising connectors positioned on a single surface to connect with fluid conduits, wherein the connectors and the fluid conduits are configured to provide introduction and removal of liquid or gaseous fluids to the plurality cell culture support layers after engagement of the clamp engagement mechanism.

3. The microphysiological system of claim 1, wherein said clamp engagement mechanism comprises a quick-release rotatable clamp to engage the top clamp component and the bottom clamp component.

4. The microphysiological system of claim 3, wherein said clamp engagement mechanism comprises a rotatable buckle connected to the bottom clamp component and said top clamp component comprises a holder.

5. The microphysiological system of claim 3, wherein:
said top clamp component comprises a holder with a plurality of orifices each configured to receive a fastener to connect said holder to a side edge of said lid;
said bottom clamp component comprises a buckle with a plurality of orifices each configured to receive a fastener to connect said bottom clamp to a side edge of said base; and
wherein said buckle is configured to reversibly engage with said holder and provide a disassembly time of less than 5 minutes to minimize an adverse biological effect on cultured biological cells during use.

6. The microphysiological system of claim 1, further comprising a plurality clamps distributed around a perimeter of said base and lid to generate said uniform contact pressure exerted on said top layer of said plurality of cell culture support layers.

7. The microphysiological system of claim 6, wherein said base and lid are multi-sided and each base-lid pair side has a clamp connected thereto.

8. The microphysiological system of claim 1, wherein each of said base and lid have sides with a side length, wherein said clamp extends over at least a central 25% of said side length.

9. The microphysiological system of claim 1, wherein said lid stepped surface comprises:
a relief feature having a relief height that is greater than or equal to 0.05 mm and less than or equal to 0.3 mm; and/or
a ratio of a relief height to thickness of the lid, from which the relief height extends, that is greater than 0.01 and less than 0.1.

10. The microphysiological system of claim 9 having a plurality of step surfaces and/or a plurality of recess surfaces.

11. The microphysiological system of claim 1, wherein said base recess surface comprises:
a step recess depth that is greater than or equal to 0.05 mm and less than or equal to 0.3 mm; and/or
a ratio of a recess height to thickness of the base, from which the recess is positioned, that is greater than 0.01 and less than 0.1.

12. The microphysiological system of claim 1, wherein:
said lid stepped surface and said base recess surface are configured to provide a deflection angle of said lid, said base, or both, that is greater than 0.1 degrees and less than 10 degrees and to maintain said uniform contact pressure against said cell culture support layers during use.

13. The microphysiological system of claim 1 having a footprint area less than or equal to 6400 mm$^2$.

14. The microphysiological system of claim 1, having a total assembled height less than or equal to 90 mm (3.5 inches).

15. The microphysiological system of claim 1, further comprising a plurality of legs connected to or extending from said base to support said base on a support surface.

16. The microphysiological system of claim 1, comprising a four-sided lid and corresponding four-sided base, with a clamp operably connected to each pair of lid and base sides.

17. The microphysiological system of claim 16, configured to receive a plurality of cell culture support layers that are circular, ellipsoid, rectangular or square.

18. The microphysiological system of claim 1, wherein said plurality of cell culture support layers comprises at least three cell cultivation layers and at least two membranes, wherein one membrane separates adjacent cell cultivation layers, wherein said cell culture layers and membranes have a total thickness that is less than or equal to 3 mm.

19. The microphysiological system of claim 18, wherein said plurality of cell culture layers comprises a lock-and-key alignment feature to align and fixably position each of said layers.

20. The microphysiological system of claim 1, having an assembly and/or disassembly time that is less than 5 minutes.

21. The microphysiological system of claim 1, further comprising access ports through a top surface of said lid for operably connecting biological sensors, controllers and/or fluidic inlets and outlets to said cell culture support layers.

22. The microphysiological system of claim 1, comprising a plurality of clamps, wherein the plurality of clamps are configured to facilitate optical imaging of cells on at least one of the cell culture support layers, optionally during use of the system, after partial disassembly of the system, or after complete removal of the cell culture support layer from the system.

23. A method of cell culturing comprising the steps of:
providing a microphysiological system of claim 1;
placing said plurality of cell culture support layers in said base;
clamping said base to said lid;
introducing biological fluid and biological cells to said cell culture support layers,
wherein said clamping step fluidically seals adjacent layers of said plurality of cell culture support layers to avoid unwanted leakage out of channels or chambers formed between adjacent cell culture support layers.

* * * * *